US012693355B2

(12) United States Patent
Huber et al.

(10) Patent No.: US 12,693,355 B2
(45) Date of Patent: Jul. 28, 2026

(54) COMPUTER-IMPLEMENTED METHOD FOR OPERATING A MAGNETIC RESONANCE FACILITY, MAGNETIC RESONANCE FACILITY, COMPUTER PROGRAM, AND ELECTRONICALLY READABLE DATA CARRIER

(71) Applicant: Siemens Healthineers AG, Forchheim (DE)

(72) Inventors: Klaus Huber, Effeltrich (DE); Volker Schnetter, Nuremberg (DE); Bernd Erbe, Lauf a.d. Pegnitz (DE)

(73) Assignee: Siemens Healthineers AG, Forchheim (DE)

( * ) Notice: Subject to any disclaimer, the term of this patent is extended or adjusted under 35 U.S.C. 154(b) by 157 days.

(21) Appl. No.: 18/658,982

(22) Filed: May 8, 2024

(65) Prior Publication Data

US 2024/0377486 A1      Nov. 14, 2024

(30) Foreign Application Priority Data

May 9, 2023      (DE) ..................... 10 2023 204 264.9

(51) Int. Cl.
*G01R 33/28* (2006.01)
*A61B 5/055* (2006.01)
(Continued)

(52) U.S. Cl.
CPC ............ *G01R 33/288* (2013.01); *A61B 5/055* (2013.01); *G01K 13/00* (2013.01); *G01R 33/543* (2013.01); *G01R 33/3403* (2013.01)

(58) Field of Classification Search
CPC ................ G01R 33/288; G01R 33/543; G01R 33/3403; A61B 5/055; G01K 13/00; G01K 2217/00; G01K 7/427
See application file for complete search history.

(56) References Cited

U.S. PATENT DOCUMENTS

| | | | |
|---|---|---|---|
| 2010/0327868 A1 | 12/2010 | Gebhardt | |
| 2014/0253117 A1* | 9/2014 | Bilu ..................... | G01R 33/422 |
| | | | 324/318 |

(Continued)

FOREIGN PATENT DOCUMENTS

| | | | | |
|---|---|---|---|---|
| CN | 105411588 A | * | 3/2016 | ............. A61B 5/055 |
| DE | 102021205916 A1 | | 12/2022 | |
| JP | 2016214277 A | * | 12/2016 | ............. A61B 5/055 |

OTHER PUBLICATIONS

English translation of JP2016214277A, provided by Espacenet. (Year: 2025).*

(Continued)

*Primary Examiner* — Rishi R Patel
(74) *Attorney, Agent, or Firm* — Lempia Summerfield Katz LLC

(57) ABSTRACT

A computer-implemented method for operating a magnetic resonance facility is provided. For thermal monitoring of an imaging component that is arranged close to a patient during an examination procedure, a monitoring value of a parameter that influences a temperature of the imaging component is ascertained in a monitoring monitor over a predefined period and is compared with a threshold value. At least one course of action is triggered when the threshold value is overshot. A plurality of monitoring monitors with different threshold values, respectively, is used for different periods.

19 Claims, 2 Drawing Sheets

(51) Int. Cl.
     *G01K 13/00*      (2021.01)
     *G01R 33/34*      (2006.01)
     *G01R 33/54*      (2006.01)

(56)                 References Cited

U.S. PATENT DOCUMENTS

2015/0285885 A1 *   10/2015   Feiweier ............... G01R 33/543
                                                                             324/309
2020/0096581 A1 *   3/2020   Pourrahimi ........ G01R 33/3815
2022/0057462 A1     2/2022   Wu

OTHER PUBLICATIONS

English translation of CN105411588A, provided by Espacenet. (Year: 2025).*
International Electrotechnical Commission. "Medical electrical equipment-Part 2-33: Particular requirements for the basic safety and essential performance of magnetic resonance equipment for medical diagnosis." IEC 60601-2-33 Ed. 3.0 (Mar. 2010). pp. 1-224.

* cited by examiner

COMPUTER-IMPLEMENTED METHOD FOR OPERATING A MAGNETIC RESONANCE FACILITY, MAGNETIC RESONANCE FACILITY, COMPUTER PROGRAM, AND ELECTRONICALLY READABLE DATA CARRIER

This application claims the benefit of German Patent Application No. DE 10 2023 204 264.9, filed on May 9, 2023, which is hereby incorporated by reference in its entirety.

BACKGROUND

The present embodiments relate to a computer-implemented method for operating a magnetic resonance facility, a magnetic resonance facility, a computer program, and an electronically readable data carrier.

In magnetic resonance imaging, nuclear spins, oriented in a main magnetic field, of an examination object (e.g., of a patient) are excited by radio-frequency pulses, and the decay in the excitation is measured as a magnetic resonance signal. For example, in the case of higher field strengths of the main magnetic field, radio-frequency pulses that are used may also have an effect on the examination object and the imaging components coming into contact with the examination object (e.g., local coils). With regard to the examination object (e.g., a patient), it is known to perform specific absorption rate (SAR) monitoring in this connection in order to provide that excessive power or energy is not input into the patient via the radio-frequency pulses. Power may be input into imaging components outside of the patient too, however. These components then heat up.

Standards, rules, and other requirements frequently exist with regard to the power input into a patient and also with regard to the heating of imaging components. The implementation of these limit the maximum radio-frequency transmission power of magnetic resonance facilities. There may be a requirement here, for example, that imaging components that are close to the patient (e.g., have at least one surface that is touching the patient and/or may be touched by the patient) should not heat up higher than a particular temperature (e.g., 41° C.).

With regard to imaging components, requirements of this kind may be implemented in the monitoring of the operation of magnetic resonance facilities in such a way that a measured variable describing the input power and thus the heating potential is ascertained or described as a monitoring value over a predefined period, with the monitoring value then being compared with a threshold value that should not be overshot and adherence to which provides that excessive heating of the imaging component does not occur. For example, it is known to choose six minutes as the length of the predefined period.

Requirements for magnetic resonance imaging demand, however, that temperatures above a particular value are not allowed to occur on surfaces that may be touched by the patient, even in the case of infinitely long examination procedures with the maximum possible power (e.g., bounded only by SAR limits, hardware limits, and software limits) and adverse load and geometry conditions. If the threshold value is adjusted in the monitoring monitor described, which over a predefined period considers a parameter as the monitoring value, such that inadmissible heating may never occur even for examination procedures that last a very long time, the consequence of this is a severe limitation of the capacity of the magnetic resonance facility.

SUMMARY AND DESCRIPTION

The scope of the present invention is defined solely by the appended claims and is not affected to any degree by the statements within this summary.

The present embodiments may obviate one or more of the drawbacks or limitations in the related art. For example, thermal monitoring of imaging components (e.g., local coils) that permits improved utilization of a capacity of the magnetic resonance facility and may still provide fulfilment of requirements is provided.

In a computer-implemented method, a plurality of monitoring monitors with different threshold values, respectively, are used for different periods.

According to this disclosure, "close to the patient" or "adjacent" may be the imaging component having at least one surface that touches the patient during the examination procedure and/or may be touched by the patient during the examination procedure. For example, it may be provided that the imaging component is a local coil. Local coils may include a plurality of receiving coil elements and may be arranged close to the patient. For example, head coils into which the head of the patient may be led for the examination procedure or coil blankets that may be placed on the patient (e.g., in the abdominal region) are known. Local coils that are to be placed under the patient have also been provided. In accordance with their purpose, local coils have conductive components and may therefore be heated by radio-frequency fields, as are generated by radio-frequency pulses. Other examples of imaging components include, for example, measuring facilities for the respiration and/or heartbeat of the patient.

A monitoring monitor may be the sum of all program means of a computer program that implements the method. This may provide ascertainment of a monitoring value (e.g., update the monitoring value, such as incorporation of the monitoring value), with which at least one corresponding threshold value is associated. The monitoring monitors may therefore also be monitoring units. Instances of the individual monitoring monitors exceeding a threshold may be established by a central monitoring unit that may carry out the comparison itself or receives or retrieves the result of the comparison from the monitoring units and, for example, in an overall view in the case of a plurality of instances of overshooting, also chooses courses of action to be carried out that may then be implemented so as to be controlled by an action unit. Overall, the method may be carried out by a control facility of the magnetic resonance facility.

Assigned to each monitoring monitor is at least one threshold value with which the monitoring value may be compared. At least the largest one of the at least one threshold value may be such a value that should not be overshot, for example, in order to reliably avoid an excessive temperature of the imaging component.

In one embodiment, the one monitoring monitor already provided in the prior art for a particular predefined period is supplemented by additional monitoring monitors (e.g., with longer predefined periods). In this way, it is possible to provide that with the overwhelming number of typically shorter magnetic resonance examinations, higher transmission power threshold values (e.g., transmission power limits) apply, and only in the case of a significantly longer duration of an examination does the transmission power have to possibly be reduced when one or more threshold values are overshot. Further, it is provided that even in the case of very long examination times and adverse load and geometry conditions, inadmissible heating of the hardware may never occur provided the highest threshold value is adhered to.

In one embodiment, it may be provided that for all monitoring monitors together, the period and/or the threshold value is chosen based on a thermal simulation of the imaging component and/or a statistical evaluation of measurement data that relates to the imaging component in order to adhere to a requirement for the admissible heating. Adherence to the requirement (e.g., in the context of an optimization method) may serve as a boundary condition. It is possible for the at least one optimization target to relate, for example, to an increase in the capacity that may be provided for examination procedures up to a certain duration. The requirement describes a limitation of the admissible heating of the imaging component (e.g., a maximum admissible temperature of the imaging component/its surfaces that are or may be touched). The maximum admissible temperature may reliably not be overshot when adhering to the highest threshold values for all monitoring monitors.

Compared with the case of an individual monitoring monitor for a single predefined period, threshold values may be set higher for certain periods (e.g., the shorter periods). The use of a plurality of monitoring monitors for different predefined periods provides more degrees of freedom for additional utilization of the capacity of the magnetic resonance facility with simultaneously reliable temperature behavior that satisfies the requirement. An optimum balance that allows significantly better measuring performance than in the case of a single monitoring monitor is thus possible.

The predefined periods may be chosen, for example, based on thermal simulations of the imaging component such that, due to the adherence to higher threshold values, the potential of still keeping the temperature of typical imaging components (e.g., local coils) low increases with thermal time constants between 5 and 20 minutes. In other words, lower threshold values may be avoided in the case of a number of (e.g., a few) short periods, and the corresponding monitoring may be shifted to longer threshold values that are possibly actually relevant only in the case of a few long examination procedures. Statistical evaluations of measurement data (e.g., field data) may be used to choose the threshold values for different predefined periods, such that examinations are affected as little as possible. In the case of longer predefined periods, the monitoring values may drop significantly (e.g., owing to the existence of breaks between different examination procedures in which no power is input via radio-frequency pulses), and the imaging component can cool down.

As already mentioned, starting from known approaches that have operated (e.g., with three to eight minutes as the predefined period), further timeframes (e.g., with longer predefined periods) are chosen. With regard to the longest period, an orientation may take place (e.g., with regard to maximum durations of examination procedures and/or thermal time constants). For example, it may be provided that for at least one monitoring monitor, the period is chosen as at least twice (e.g., at least three times) the thermal time constant of the imaging component. In this way, even transient phenomena on longer time scales are adequately covered.

In a specific embodiment, it may be provided that for at least one monitoring monitor of the plurality of monitoring monitors, the period is chosen from the group including: a period in the region of three to eight minutes; a period in the region of ten to fifteen minutes; a period in the region of eighteen to twenty five minutes; and a period in the region of forty to sixty minutes.

While, for example, three to six monitoring monitors may be provided in order to reach a good compromise between expenditure and degrees of freedom obtained in the monitoring, four monitoring monitors may be used in a specific example. For example, predefined periods of 6 minutes, 12 minutes, 20 minutes, and 50 minutes may be used in this connection.

In one embodiment, a mean over the predefined period as a sliding timeframe may be ascertained as the monitoring value. The mean may refer to the parameter or a value derived herefrom (e.g., a value proportional to the input power). The mean may represent a statistical result that is also comparable for different predefined periods. Alternatively, in one embodiment, a summation/integration or the like may be used.

In one embodiment, the parameter describes a power, input into the imaging component, of at least one radio-frequency pulse of the examination procedure. The examination procedure may include one or more recording protocols that may use one or more magnetic resonance sequences, respectively. The radio-frequency pulses of these magnetic resonance sequences (e.g., excitation pulses and the like) represent the main source for the heating of imaging components in the patient receiver. The power input by such radio-frequency pulses represents a measure of the heating that occurs. The power and/or parameters describing the power are therefore particularly suitable for thermal monitoring.

In one embodiment, all monitoring monitors monitor the same parameter or the same monitoring value. For example, a measure for the power emitted by a transmission coil arrangement, which may be ascertained as the difference in the ingoing and the outgoing power, may be used directly; in example embodiments, it may additionally or alternatively also be advantageous to use the square of the field strength of the radio-frequency excitation field. While the B1+ fraction (e.g., the fraction of the radio-frequency excitation field effective for the magnetic resonance imaging) serves as the design basis for the magnetic resonance sequences and is often immediately known (e.g., for advance calculations), it is the squared value of the total radio-frequency excitation field ($B1tot^2$) that is primarily responsible for the heating of the imaging component (e.g., the local coil). The total radio-frequency excitation field results due to unavoidable B1 fractions of the radio-frequency excitation field that are not effective for the magnetic resonance imaging and as a general rule: $B1tot^2 >= B1+^2$.

If it is not immediately possible to monitor the squared value of the total radio-frequency excitation field, therefore, it is not possible to ascertain a corresponding monitoring value (e.g. a mean); the correlation with the maximum possible heating may be estimated via proportionality constants that are dimensioned for the worst case. If, for example, a magnetic resonance facility with a main magnetic field strength of 3 tesla is considered, $B1tot^2$ may be nearly 60% higher than $B1+^2$ in adverse cases in the CP excitation mode. When using B1+ as a parameter, therefore, an increase of 60% with respect to $B1+^2$ may be assumed even if the actual fraction of B1, and therewith also the heating of the imaging component, would be significantly lower in practice.

In a development of the present embodiments, it may be provided that for each pending examination procedure, over its duration, immediately before the beginning of the examination procedure, the parameter, and thus the monitoring value, is calculated in advance for all monitoring monitors, and the monitoring values calculated in advance are compared with the threshold values. When at least one threshold value is overshot, the at least one course of action takes place instead of the beginning of the examination procedure. In one embodiment, monitoring therefore takes place as a prediction at the start of an examination procedure by using the history of the respective monitoring value, incorporated by the respective monitoring monitor, and the recording parameter for the examination procedure that should currently be started. For example, when using field values of the radio-frequency excitation field as parameters, it is also possible to use adjustment results for the advance calculation for the examination procedure that may currently be started. As already mentioned, the examination procedure may include at least one recording protocol (e.g., measuring protocol), so the recording parameters may be, for example, protocol parameters. The advance calculation may take place, for example, via the "rolling out" of magnetic resonance sequences and/or may be ascertained via mathematical correlations (e.g., limited to the radio-frequency pulses). Corresponding advance calculation techniques have already been provided in the prior art.

If the parameter may be calculated in advance, then this also applies to the monitoring value (e.g., in that with a sliding mean, the timeframe of the length of the predefined period is shifted further into the region of the duration of the examination that has been calculated in advance). In this connection, it is possible to ascertain monitoring values as the characteristic over the duration of the examination, as well as to choose particular instants including at least the end of the duration of the examination.

If overshooting of the threshold value (e.g., of the highest threshold value) is established for at least one monitoring monitor, which indicates potential excessive heating of the imaging component, the output of a warning message to a user and/or querying of a user input as to whether the examination procedure should still be started may be used as the course of action that is carried out instead of the beginning of the examination procedure. The user may therefore be made aware of the risk of excessive heating of the imaging component, which is not in accordance with the requirement, but may, for example, still decide for themselves whether the examination procedure should be carried out anyway. This may be provided, for example, if a particular short-lived preparation of the patient (e.g., administration of a contrast medium) has been performed and the requirement (e.g., the maximum temperature) was chosen such that a slight overshooting does not result in risks to the patient.

In an embodiment, it may also be provided that as a course of action, a waiting time and/or at least one adjusted recording parameter is ascertained for the examination procedure and is output to a user as a recommendation. The recommendations may be specified (e.g., for the waiting time and/or in an imaging component-specific manner) or may also be ascertained by taking into account the at least one overshot threshold value and/or at least one thermal property of the at least one imaging component and/or the recording parameter of the examination procedure. A waiting time may be provided for the imaging component to be able to cool somewhat again. The waiting time may be firmly specified, but, for example, at least in an imaging component-specific manner, so, for example, thermal time constants may be taken into account. An adjustment of the recording parameters in order to react to the potential overshooting of the heating limits may be provided in order to prevent this potential overshooting. In this connection, at least one further advance calculation, for example, may take place with modified recording parameters, and it is possible to again check whether at least one of the highest threshold values is being overshot.

While such an advance calculation may be provided in order to be able to provide a forewarning even before starting an examination procedure, continuous real-time monitoring (e.g., online monitoring) based on, for example, current operating data may be provided alternatively or additionally. Since the actual temporal development of the parameter is to be tracked anyway for the monitoring monitors in the case of advance calculation in order to have the history (e.g., actual history) available, current operating data is obviously also continually used for this case.

In a development of the present embodiments, with continuous real-time monitoring using current operating data, when at least one threshold value is overshot during an examination procedure, a termination of the examination procedure and/or querying of a user as to whether the examination procedure should be terminated takes place as a course of action.

This provides that measuring terminations may occur with online monitoring if the threshold values (e.g., highest threshold values) are overshot during the runtime. For example, when a maximum admissible temperature of the imaging component is carefully chosen anyway, however, so harmful effects on the patient are not to be expected when the threshold is slightly overshot, a user may be permitted to continue the examination procedure, as in the case of the advance calculation.

In an embodiment, it may be provided that as one or more of the at least one courses of action, a cooling means (e.g., a cooling device), acting on the imaging component, of the magnetic resonance facility is actuated to increase the cooling power. In this way, the monitoring monitors also serve for appropriate actuation of cooling means that act on the imaging component. This provides that while using the monitoring monitors, the cooling means is only operated when it is also expedient to do so. For example, the cooling means may be a ventilation facility (e.g., a fan) for the patient receiver of the magnetic resonance facility. The coupling of the cooling means operation to the monitoring monitors also allows threshold values to be set higher since the active cooling measures may then be taken into account. In other words, when the results of the monitoring monitors (e.g., the advance calculation) are coupled with further courses of action for reducing the temperature, such as with active venting of the patient receiver with a fan, the threshold values may be increased further without having to worry about inadmissible heating. The probability of limiting particular examinations is reduced significantly as a result.

In this connection, a plurality of threshold values may be provided for each monitoring monitor, with the highest threshold value continuing to represent the limit value that indicates the risk of excessive heating and is not to be overshot. Cooling agents may be activated before the occurrence of the critical case, however, or before the occurrence in a critical region, so, for example, a further threshold value may be provided at 70 to 90% (e.g., 80%) of the highest threshold value, on attainment of which the cooling means is activated or is actuated for increased cooling. In such a case the actuation of the cooling means may be associated with the attainment of the lower threshold value, while attainment of the highest threshold value may result, for example, in warnings or the like.

In a specific embodiment, it may be provided, for example, that the cooling means has cooling levels associated with different cooling powers. For at least one monitoring monitor of the plurality of monitoring monitors, a plurality of threshold values is used with which different cooling levels to be activated are associated. A remaining portion of the plurality of threshold values may result as a percentage of a highest threshold value of the threshold values, for example. Purely by way of example, the cooling means may be activated at a first cooling level when 20% of the highest threshold value is attained, may be switched to a second cooling level when 50% of the highest threshold value is attained, and may be switched to a third cooling level when 80% of the highest threshold value is attained.

With different examination procedures (e.g., different patients), the situation may also occur where imaging components close to the patient are replaced, added, or removed. For example, a different local coil may be required for the following patient than for the current patient. In such cases for imaging components that are to be thermally monitored, their current situation close to the patient respectively may be tracked.

In one embodiment, it may be provided that for one or more imaging components that are to be thermally monitored of the at least one imaging component, of which use in an examination procedure may be automatically established (e.g., via a connection means), it is only when the imaging component is used in an examination procedure that contributions of the parameter from the examination procedure are included in the monitoring monitors. For example, for local coils as the imaging components, it is known that the local coils are identified by connection via their coil plug as soon as the local coils are inserted in a plug-in location of a patient couch of the magnetic resonance facility. This and comparable items of information may be used to establish whether an imaging component is currently arranged close to the patient or may cool outside of the patient receiver.

In addition to the method, the present embodiments also relate to a magnetic resonance facility (e.g., a magnetic resonance device), having an imaging component (e.g., an imaging device), that is arranged close to (e.g., adjacent to) the patient during an examination procedure, and a control facility (e.g., a controller) that is configured for carrying out a method of the present embodiments. All statements with respect to the method of the present embodiments may be transferred analogously to the magnetic resonance facility of the present embodiments, with which the advantages may therefore likewise be achieved.

The magnetic resonance facility may have, for example, a main magnetic unit that includes the main magnet generating the main magnetic field, and may have a cylindrical patient receiver into which a patient may be moved by a patient couch, on which the at least one imaging component to be thermally monitored (e.g., a local coil) may also be placed close to the patient. The control facility, which controls operation of the magnetic resonance facility, may have, for example, at least one processor and at least one storage means (e.g., at least one storage device). The control facility may also include functional units implemented by hardware and/or software in order to carry out acts of the method of the present embodiments.

In one embodiment, it may be provided, for example, that the control facility includes: a plurality of monitoring monitors (e.g., monitoring units) for respectively ascertaining a monitoring value of at least one parameter that affects the temperature of the imaging component, over a respective predefined period; a monitoring unit for establishing a comparison result of the different monitoring values with a threshold value associated with the respective monitoring monitor; and an action unit for carrying out at least one course of action when the threshold value is overshot for at least one monitoring monitor. Different threshold values and different predefined periods respectively are associated with the plurality of monitoring monitors.

The comparison may be carried out in the respective monitor unit but also by the monitoring unit.

A computer program of the present embodiments may be loaded directly into a storage means (e.g., a storage device) of a control facility of a magnetic resonance facility and has program means that prompt the control facility to carry out the acts of a method of the present embodiments when the computer program is executed. The computer program may be stored on an electronically readable data carrier (e.g., a non-transitory computer-readable storage medium) according to the present embodiments. The electronically readable data carrier may therefore include items of control information stored thereon that include at least one computer program of the present embodiments and are configured such that when the data carrier is used in a control facility of a magnetic resonance facility, the control facility is configured to carry out a method of the present embodiments.

DETAILED DESCRIPTION

Figure 1:
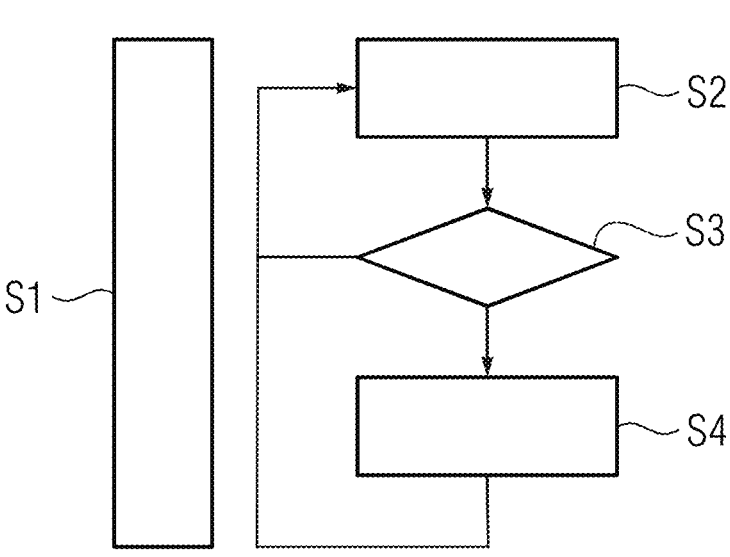
FIG. 1 shows a flowchart of an example embodiment of a method.

FIG. 1 shows a flowchart of an example embodiment of a method. In addition to possibly further monitoring processes (e.g., SAR monitoring), monitoring monitors are continually used in act S1 during operation of a magnetic resonance facility in order to thermally monitor an imaging component that may be placed close to the patient during the examination procedures. For example, it should be provided that the imaging component does not overshoot a maximum temperature (e.g., 41° C.) at surfaces that touch the patient to be examined and/or may be touched by the patient. In the present case, the imaging component is a local coil placed, for example, on, at, or under the patient.

A plurality of monitoring monitors (e.g., four monitoring monitors) are used in this connection to ascertain respectively the same monitoring value of a parameter that describes power input into the imaging component due to radio-frequency pulses, and to keep the monitoring value of the parameter up-to-date, with each monitoring monitor relating to a different predefined period. Specifically, in the present case, the field strength of the total radio-frequency excitation field is regarded as the parameter, the square proportional to the power is ascertained herefrom, and a sliding mean is ascertained over the respective predefined period in the manner of a sliding timeframe. The predefined periods may therefore also be understood as different averaging windows. This incorporation during and between examination procedures occurs based on actual operating data of the magnetic resonance facility. Alternatively or in addition, a B1+ fraction of the radio-frequency excitation field and/or the ingoing and the outgoing power of the transmission coil arrangement utilized may also be used as the parameters, with a proportionality factor that describes a Worst Case scenario of $B1+^2$ to $B1tot^2$ being applied when ascertaining the monitoring value when the B1+ fraction is used.

At least one threshold value is associated with each monitoring monitor, with a highest threshold value of this at least one threshold value representing the limit that should not be exceeded since otherwise, excessive heating of the imaging component (e.g., above the maximum temperature) may be provided. The predefined periods are chosen, for example, based on thermal simulations and/or by taking into account the thermal time constants of the imaging component, such that new, further degrees of freedom result for the threshold values. This allows these threshold values to be set higher, at least for the shorter periods, and still provide that no excessive heating of the imaging component occurs. In the present case, for example, six minutes, twelve minutes, twenty minutes, and fifty minutes are used. The (highest) threshold values may be chosen in this connection, also while using statistical evaluations of field data, such that the capacity of the magnetic resonance facility (e.g., the measuring performance) is to be limited as little as possible. Further, it may still be provided that no inadmissible heating occurs.

Act S2 is then carried out if a new examination procedure (e.g., including at least one recording protocol with at least one magnetic resonance sequence respectively) is to be started. Then, using the recording parameter describing the examination procedure, it is calculated in advance how the monitoring values of the monitoring monitors will develop over the duration of the examination procedure. In other words, the known history of the parameter and of the monitoring value, as results in act S1, is used together with an advance calculation of the examination procedure to predict the sliding mean via shifting of the respective predefined period into the duration of the examination procedure. The result of act S2 may be a characteristic of the monitoring value over the duration of the examination procedure but also solely a result for chosen instants (e.g., including the end of the examination procedure).

In act S3, it is then checked whether, based on the advance calculation, the threshold values associated with the respective monitoring monitors are exceeded by the examination procedure. At least one particular course of action to be carried out may be associated with each instance of overshooting and/or combination thereof in this connection. If there is at least one instance of overshooting, the corresponding at least one course of action is carried out in act S4.

If the highest threshold value, the overshooting of which therefore describes the risk of inadmissible heating of the imaging component, is overshot, a warning message that shows the user the impending overheating is output as a course of action in each case, together with a suggestion for a waiting time that should still be allowed to elapse. The user may accordingly accept the suggestion by user input and allow the waiting time to elapse, during which the imaging component may cool, but also decide that the examination procedure should still be carried out as planned. In example embodiments, recording parameters of the examination procedure with which the risk does not exist may be suggested. In one embodiment, the user may decide to accept the suggestion or to still start the examination procedure unchanged. The waiting time may be imaging component-specific and thus take into account, for example, thermal time constants of the imaging component.

While it is basically conceivable to associate just one (e.g., the highest) threshold value that is not to be overshot with each monitoring monitor, it is also possible to use further threshold values for at least one monitoring monitor. These may be chosen, for example, as a percentage of the highest threshold value. As courses of action, when an instance of overshooting of such a further threshold value has been established in act S3, cooling means that act on the imaging component (e.g., a fan for active ventilation of the patient receiver) may be actuated in act S4 (e.g., may be activated in the case of lower threshold values and then be switched to higher cooling levels in the case of higher threshold values).

Further, in addition to the advance calculation and checking at the start of an examination procedure, it is also possible to carry out real-time monitoring. This provides checking the monitoring of the threshold values based on the continual updating of the monitoring values in act S1. The continual updating is based on operating data. Courses of action when the highest threshold value is overshot may then also include a termination of the examination procedure in the extreme case or else trigger querying of a user as to whether measuring should continue. In each case, a warning message may be issued too.

The method may be carried out for a plurality of imaging components (e.g., also while using the same monitoring values), but possibly different imaging component-specific threshold values. In this connection, it may also easily be established in the case of local coils whether a particular local coil is being used as an imaging component in an examination procedure. The radio-frequency excitation field may thus induce heating during the examination procedure. Such an item of information may be ascertained, for example, based on the insertion or removal of a coil plug in a plug-in location of the patient couch.

Figure 2:
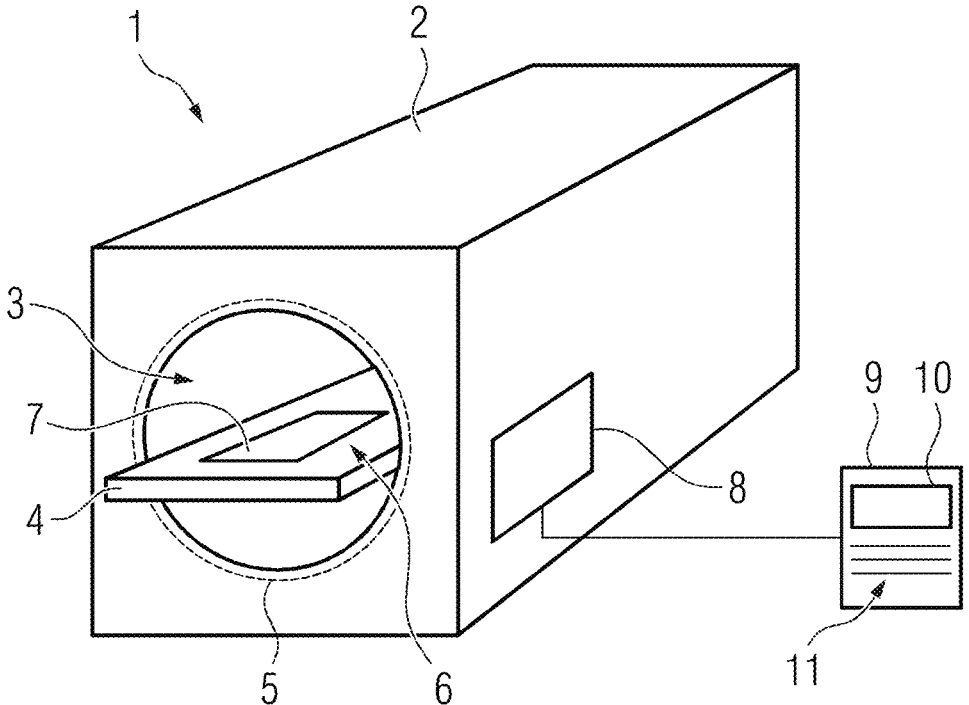
FIG. 2 shows a schematic diagram of an embodiment of a magnetic resonance facility.

FIG. 2 shows a schematic diagram of an embodiment of a magnetic resonance facility 1. The magnetic resonance facility 1 includes a main magnetic unit 2 that defines a cylindrical patient receiver 3 into which a patient may be moved on a patient couch 4 for examination. In addition to a gradient coil arrangement (not shown), a radio-frequency coil arrangement (e.g., a body coil) is also arranged as a transmission coil arrangement 5 so as to surround the patient receiver 3. During examination procedures, radio-frequency pulses are output via the transmission coil arrangement 5 and generate the radio-frequency excitation fields. A local coil 7 is indicated on the patient couch 4 as an imaging component 6.

Operation of the magnetic resonance facility 1 is controlled by a control facility 8 that is also configured for carrying out the method of the present embodiments. To be able to receive user inputs and/or output warning messages, the control facility 8 is connected to an operator facility 9 that includes an output facility 10 and an input facility 11.

Figure 3:
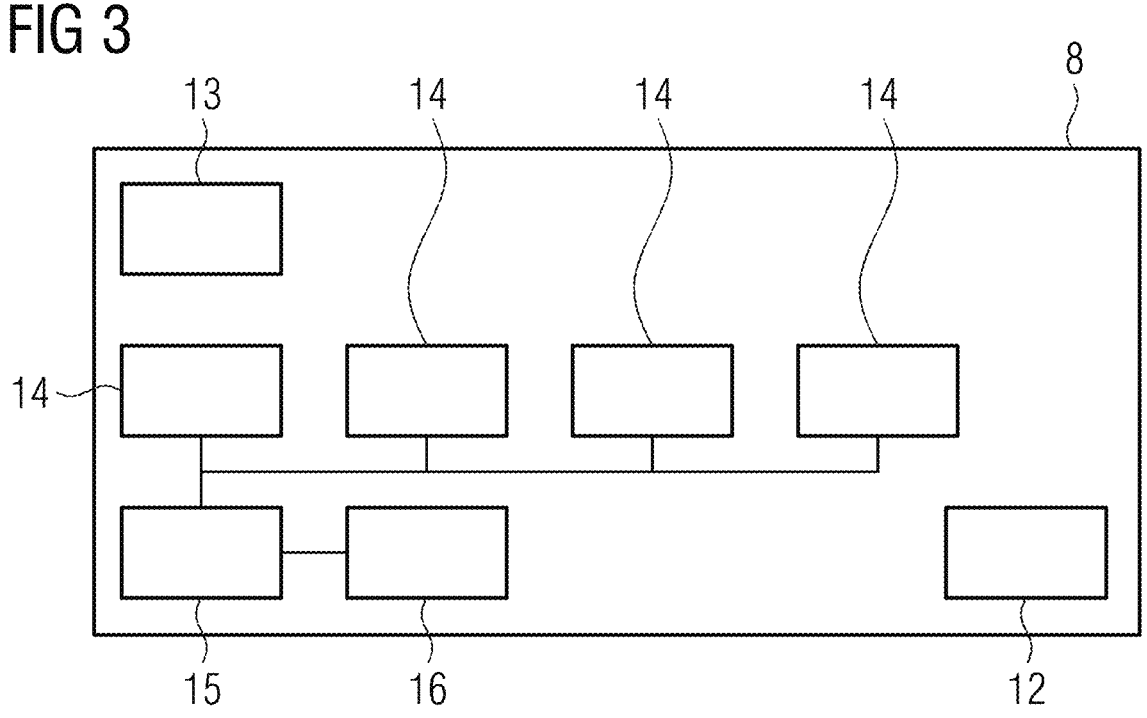
FIG. 3 shows the functional construction of a control unit of the magnetic resonance facility.

FIG. 3 shows the functional construction of the control facility 8 in more detail. First, this has a storage device 12 in which items of information (e.g., measured variables, monitoring values, and their history) may be stored. The examination operation during examination procedures is controlled by a basically known sequence unit 13.

For implementing the method of the present embodiments, the control facility 8 first has the four monitoring monitors 14 that may also be referred to as monitoring units. In accordance with act S1, the four monitoring monitors 14 continuously ascertain the respective monitoring values. The four monitoring monitors 14 may also be configured (e.g., by a corresponding advance calculation subunit) to carry out act S2. A monitoring unit 15 establishes the comparison results of act S3, with it being possible for the comparison to occur there specifically or else also in the monitoring monitors 14 already. The courses of action triggered by the monitoring unit 15 are carried out by an action unit 16.

Although the invention has been illustrated and described in detail by the example embodiments, the invention is not limited by the disclosed examples, and a person skilled in the art may derive other variations herefrom without departing from the scope of the invention.

Independent of the grammatical term usage, individuals with male, female or other gender identities are included within the term.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a magnetic resonance facility, the method being computer-implemented and comprising:

for thermal monitoring of at least one imaging component that is arranged adjacent to a patient during an examination procedure, ascertaining a monitoring value of at least one parameter that influences a temperature of the at least one imaging component in at least one monitoring monitor of a plurality of monitoring monitors over a predefined period, wherein the predefined period is different for all monitoring monitors of the plurality of monitoring monitors, respectively;

comparing the monitoring value with a threshold value, wherein the threshold value is different for all monitoring monitors of the plurality of monitoring monitors, respectively; and triggering at least one course of action when, based on the comparing, the monitoring value is greater than the threshold value, wherein, during the thermal monitoring of the at least one imaging component, it is ensured that a surface of the at least one imaging component touching or touchable by the patient does not overshoot a maximum temperature.

2. The method of claim 1, wherein:

for all monitoring monitors of the plurality of monitoring monitors together, respectively, the predefined period, the threshold value, or the predefined period and the threshold value are chosen based on a thermal simulation of the at least one imaging component, a statistical evaluation of measurement data that relates to the at least one imaging component, or a combination thereof, such that a requirement for admissible heating is adhered to;

for the at least one monitoring monitor of the plurality of monitoring monitors, the predefined period is chosen as at least twice a thermal time constant of the at least one imaging component; or a combination thereof.

3. The method of claim 2, wherein the predefined period is at least three times the thermal time constant of the at least one imaging component.

4. The method of claim 1, wherein for the at least one monitoring monitor of the plurality of monitoring monitors, the predefined period is:

a period in a region of three to eight minutes;

a period in a region of ten to fifteen minutes;

a period in a region of eighteen to twenty-five minutes; or a period in a region of forty to sixty minutes.

5. The method of claim 1, wherein a mean over the predefined period as a sliding timeframe is ascertained as the monitoring value.

6. The method of claim 1, wherein the at least one parameter describes a power, input into the at least one imaging component, of at least one radio-frequency pulse of the examination procedure.

7. The method of claim 1, wherein for each pending examination procedure, over a duration, immediately before a beginning of the respective pending examination procedure, the at least one parameter, and thus the monitoring value, is calculated in advance for all monitoring monitors of the plurality of monitoring monitors, and the monitoring values calculated in advance are compared with the different threshold values, respectively, and wherein the at least one course of action takes place instead of the beginning of the examination procedure when at least one of the different threshold values is overshot.

8. The method of claim 7, wherein the course of action comprises outputting a warning message to a user, querying a user input, according to which the examination procedure should still be started, or a combination thereof.

9. The method of claim 7, wherein the course of action comprises ascertaining a waiting time, at least one adjusted recording parameter, or the waiting time and the at least one adjusted recording parameter for the examination procedure, and outputting the waiting time, the at least one adjusted recording parameter, or the waiting time and the at least one adjusted recording parameter to a user as a recommendation.

10. The method of claim 1, wherein with continuous monitoring using current operating data, when the threshold value is overshot during an examination procedure, a termination of the examination procedure, querying of a user as to whether the examination procedure should be terminated, or a combination thereof takes place as a course of action of the at least one course of action.

11. The method of claim 1, wherein the at least one course of action comprises actuating a cooling means, acting on the at least one imaging component, of the magnetic resonance facility, such that cooling power is increased.

12. The method of claim 11, wherein the cooling means has cooling levels associated with different cooling powers, wherein for the at least one monitoring monitor of the plurality of monitoring monitors, a plurality of threshold values is used, with which different cooling levels that are to be activated are associated.

13. The method of claim 1, wherein for one or more imaging components of the at least one imaging component that are to be thermally monitored and for which use in an examination procedure is automatically establishable, it is only when the one or more imaging components are used in the examination procedure that contributions of the at least one parameter from the examination procedure are included in the plurality of monitoring monitors.

14. The method of claim 13, wherein use of the one or more imaging components in the examination procedure is automatically establishable via a connection means.

15. A magnetic resonance facility comprising:
an imaging component that is arranged adjacent to a patient during an examination procedure; and
a controller configured for operating the magnetic resonance facility, the controller being configured for operating the magnetic resonance facility comprising the controller being configured to:
for thermal monitoring of the imaging component, ascertain a monitoring value of at least one parameter that influences a temperature of the imaging component in at least one monitoring monitor of a plurality of monitoring monitors over a predefined period, wherein the predefined period is different for all monitoring monitors of the plurality of monitoring monitors, respectively;
compare the monitoring value with a threshold value, wherein the threshold value is different for all monitoring monitors of the plurality of monitoring monitors, respectively; and
trigger at least one course of action when, based on the comparison, the monitoring value is greater than the threshold value,
wherein, during the thermal monitoring of the at least one imaging component, it is ensured that a surface of the at least one imaging component touching or touchable by the patient does not overshoot a maximum temperature.

16. In a non-transitory computer-readable storage medium that stores instructions executable by one or more processors to operate a magnetic resonance facility, the instructions comprising:
for thermal monitoring of at least one imaging component that is arranged adjacent to a patient during an examination procedure, ascertaining a monitoring value of at least one parameter that influences a temperature of the at least one imaging component in at least one monitoring monitor of a plurality of monitoring monitors over a predefined period, wherein the predefined period is different for all monitoring monitors of the plurality of monitoring monitors, respectively;
comparing the monitoring value with a threshold value, wherein the threshold value is different for all monitoring monitors of the plurality of monitoring monitors, respectively; and
triggering at least one course of action when, based on the comparing, the monitoring value is greater than the threshold value,
wherein, during the thermal monitoring of the at least one imaging component, it is ensured that a surface of the at least one imaging component touching or touchable by the patient does not overshoot a maximum temperature.

17. The non-transitory computer-readable storage medium of claim 16, wherein:
for all monitoring monitors of the plurality of monitoring monitors together, respectively, the predefined period, the threshold value, or the predefined period and the threshold value are chosen based on a thermal simulation of the at least one imaging component, a statistical evaluation of measurement data that relates to the at least one imaging component, or a combination thereof, such that a requirement for admissible heating is adhered to;
for the at least one monitoring monitor of the plurality of monitoring monitors, the predefined period is chosen as at least twice a thermal time constant of the at least one imaging component; or
a combination thereof.

18. The non-transitory computer-readable storage medium of claim 16, wherein for the at least one monitoring monitor of the plurality of monitoring monitors, the predefined period is:
a period in a region of three to eight minutes;
a period in a region of ten to fifteen minutes;
a period in a region of eighteen to twenty-five minutes; or
a period in a region of forty to sixty minutes.

19. The non-transitory computer-readable storage medium of claim 16, wherein a mean over the predefined period as a sliding timeframe is ascertained as the monitoring value.

* * * * *